(12) United States Patent
Rashid (10) Patent No.: US 11,529,477 B2
(45) Date of Patent: Dec. 20, 2022

(54) ELECTRONIC SMOKING DEVICE WITH WICKLESS ATOMIZER

(71) Applicant: Fontem Holdings 1 B.V., Amsterdam (NL)

(72) Inventor: Muneeb Rashid, Hamburg (DE)

(73) Assignee: Fontem Ventures B.V., Amsterdam (NL)

(*) Notice: Subject to any disclaimer, the term of this patent is extended or adjusted under 35 U.S.C. 154(b) by 325 days.

(21) Appl. No.: 15/765,250

(22) PCT Filed: Oct. 5, 2016

(86) PCT No.: PCT/EP2016/073751
§ 371 (c)(1),
(2) Date: Mar. 30, 2018

(87) PCT Pub. No.: WO2017/060279
PCT Pub. Date: Apr. 13, 2017

(65) Prior Publication Data
US 2018/0279680 A1    Oct. 4, 2018

(30) Foreign Application Priority Data
Oct. 5, 2015   (EP) .................................... 15188353

(51) Int. Cl.
*A61M 15/06*    (2006.01)
*A61M 11/04*    (2006.01)
(Continued)

(52) U.S. Cl.
CPC ............. *A61M 15/06* (2013.01); *A24F 40/46* (2020.01); *A24F 40/485* (2020.01);
(Continued)

(58) Field of Classification Search
CPC ..................................................... A24F 47/008
See application file for complete search history.

(56) References Cited

U.S. PATENT DOCUMENTS

2014/0270730 A1* 9/2014 DePiano ............... A24F 47/008
392/404

FOREIGN PATENT DOCUMENTS

| CN | 203986096 U | 12/2014 |
|---|---|---|
| CN | 104824853 A | 8/2015 |

OTHER PUBLICATIONS

English language machine translation of CN-104824853-B (Year: 2018).*
Machine translation of CN 104824853 (Year: 2021).*

* cited by examiner

*Primary Examiner* — Kelly M Gambetta
*Assistant Examiner* — Jennifer A Kessie
(74) *Attorney, Agent, or Firm* — Dykema Gossett PLLC (57) ABSTRACT

An electronic smoking device is provided including a power supply portion comprising a power supply, an atomizer/liquid reservoir portion comprising a liquid reservoir storing a liquid, and an atomizer adapted to atomize the liquid stored in the liquid reservoir when operated by the power supply. The atomizer extends away from the liquid reservoir in a first direction (L). The atomizer comprises first atomizer sections, wherein each of the first atomizer sections defines an opening that is at least partly encircled by the first atomizer section. The sizes of the openings defined by the first atomizer sections decrease with increasing distance of the first atomizer sections from the liquid reservoir in the first direction.

12 Claims, 4 Drawing Sheets

(51) Int. Cl.
*A24F 40/46* (2020.01)
*A24F 40/485* (2020.01)
*A61M 16/00* (2006.01)
*A24F 40/10* (2020.01)
*H05B 3/42* (2006.01)
*H05B 6/36* (2006.01)

(52) U.S. Cl.
CPC ............ *A61M 11/042* (2014.02); *A24F 40/10* (2020.01); *A61M 2016/0021* (2013.01); *A61M 2205/3317* (2013.01); *A61M 2205/3331* (2013.01); *A61M 2205/3375* (2013.01); *A61M 2205/3653* (2013.01); *A61M 2205/8206* (2013.01); *H05B 3/42* (2013.01); *H05B 6/36* (2013.01)

ELECTRONIC SMOKING DEVICE WITH WICKLESS ATOMIZER

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

In order to ensure constant operability of the electronic smoking device, the atomizer has to be reliably supplied with liquid to be atomized.

SUMMARY OF THE INVENTION

In accordance with one aspect of the present invention there is provided an electronic smoking device including a power supply portion comprising a power supply, an atomizer/liquid reservoir portion comprising a liquid reservoir storing a liquid, and an atomizer adapted to atomize the liquid stored in the liquid reservoir when operated by the power supply. The atomizer extends away from the liquid reservoir in a first direction. The atomizer comprises first atomizer sections, wherein each of the first atomizer sections defines an opening that is at least partly encircled by the first atomizer section. The sizes of the openings defined by the first atomizer sections decrease with increasing distance of the first atomizer sections from the liquid reservoir in the first direction.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
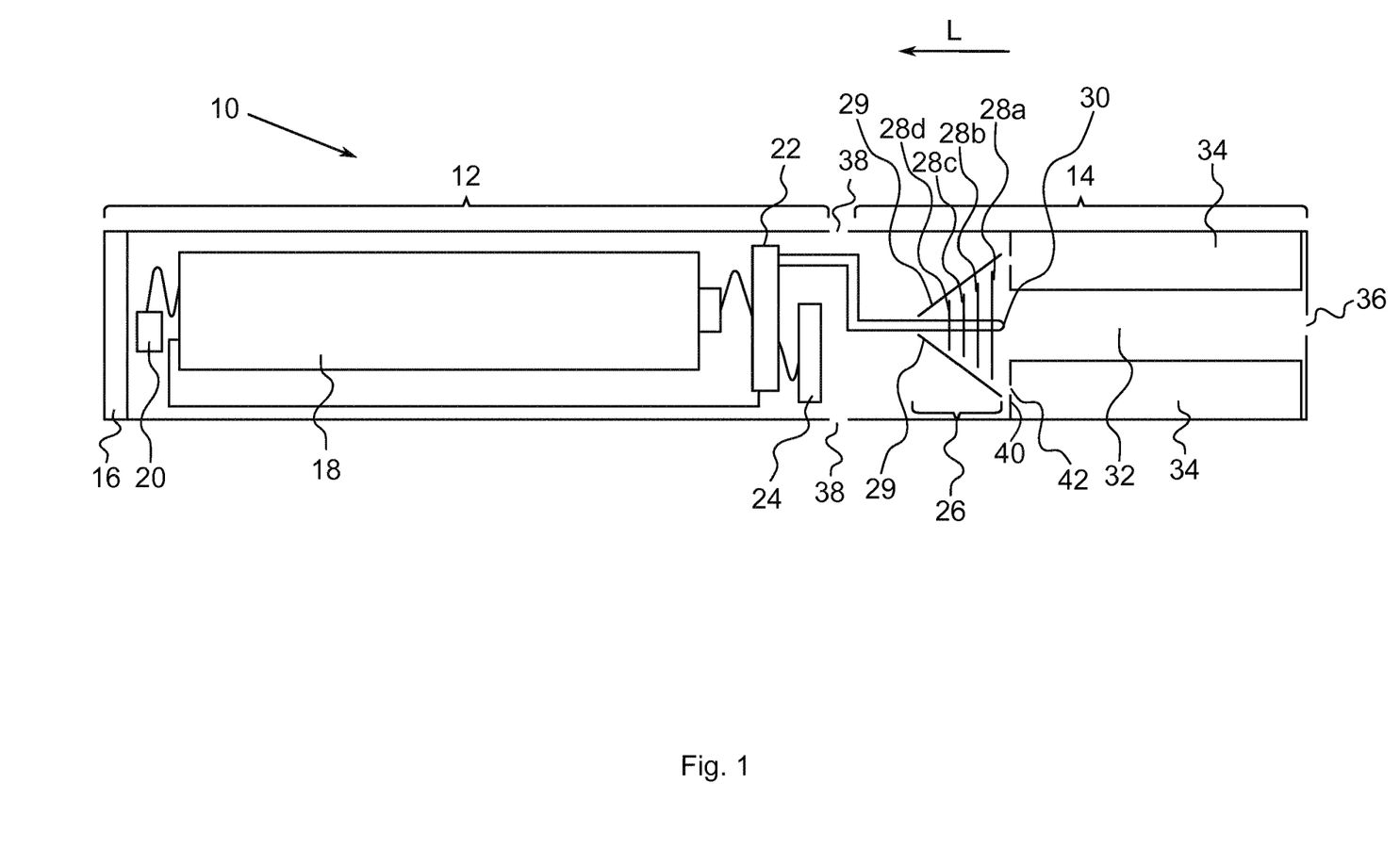
FIG. 1 is a schematic cross-sectional illustration of an exemplary e-cigarette.

Throughout the following, an electronic smoking device will be exemplarily described with reference to an e-cigarette. As is shown in FIG. 1, an electronic smoking device 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a power supply portion 12 and an atomizer/liquid reservoir portion 14. Together the power supply portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 180 mm, and diameters from 5 to 20 mm.

The power supply portion 12 and atomizer/liquid reservoir portion 14 are typically made of metal, e.g. steel or aluminum, or of hardwearing plastic and act together with the end cap 16 to provide a housing to contain the components of the e-cigarette 10. The power supply portion 12 and an atomizer/liquid reservoir portion 14 may be configured to fit together by a friction push fit, a snap fit, or a bayonet attachment, magnetic fit, or screw threads. The end cap 16 is provided at the front end of the power supply portion 12. The end cap 16 may be made from translucent plastic or other translucent material to allow an LED 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 12 and the atomizer/liquid reservoir portion 14. FIG. 1 shows a pair of air inlets 38 provided at the intersection between the power supply portion 12 and the atomizer/liquid reservoir portion 14.

A battery 18, a light-emitting diode (LED) 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the electronic smoking device 10. The airflow sensor 24 can be any suitable sensor for detecting changes in airflow or air pressure, such as a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating element 30 which extends into a cone-shaped casing 29 of the atomizer 26, which casing 29 partially encases a plurality of first atomizer sections 28a, 28b, 28c, 28d. These first atomizer sections 28a, 28b, 28c, 28d are configured to receive and hold liquid supplied from a liquid reservoir 34 through openings 42 in a base plate 40 of the liquid reservoir 34 before the liquid is aerosolized by operation of the heating element 30. In combination, the first atomizer sections 28a, 28b, 28c, 28d are configured to replace a conventional wick, as described with reference to FIG. 2 in more detail below, together with the structure and functionality of the atomizer 26. The atomizer 26 extends away from the liquid reservoir 34 in a first direction that corresponds to the longitudinal direction L of the electronic smoking device 10.

Figure 2:
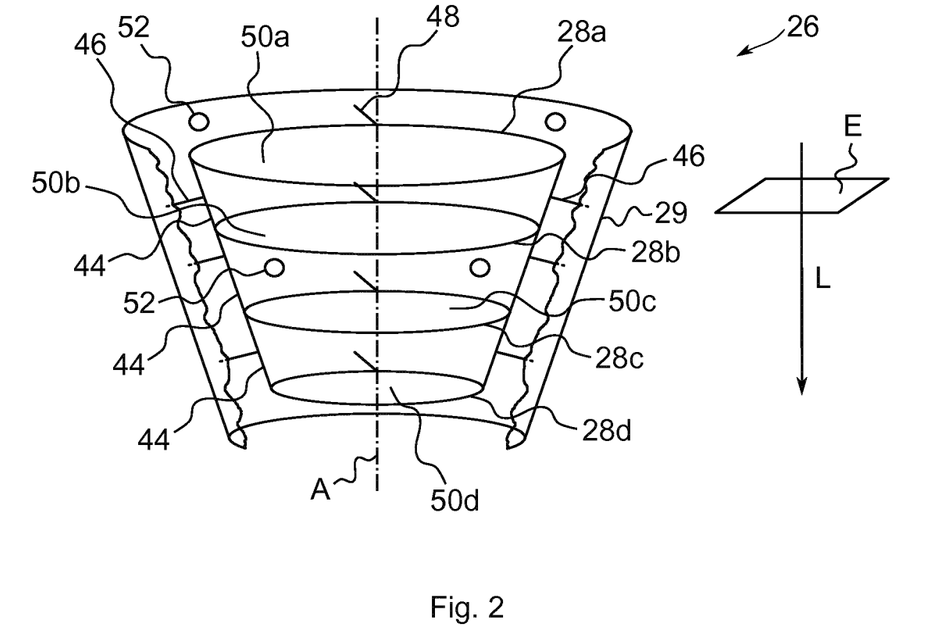
FIG. 2 is a partial perspective illustration of an atomizer according to a first embodiment.

The atomizer 26 is located adjacent to one end of a central passage 32 of the atomizer/liquid reservoir portion 14, which central passage 32 is surrounded by the cylindrical liquid reservoir 34. The atomizer 26 does not completely block the central passage 32. Rather air gaps are provided in the cone shaped atomizer casing 29, in particular at the apex, enabling air to flow past the heating element 30. Further air inlet openings 52 can be provided in the wall portions of the casing 29, as shown in FIG. 2. The atomizer may alternatively use other forms of heating elements, such as ceramic heaters, or fiber or mesh material heaters. Nonresistance heating elements such as sonic, piezo and jet spray may also be used in the atomizer in place of the heating coil.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or maybe formed in an end cap.

In use, a user sucks on the electronic smoking device 10. This causes air to be drawn into the electronic smoking device 10 via one or more air inlets, such as air inlets 38, and to be drawn through the central passage 32 towards the air inhalation port 36. The change in air pressure which arises is detected by the airflow sensor 24, which generates an electrical signal that is passed to the control electronics 22. In response to the signal, the control electronics 22 activate the heating element 30, which causes liquid present in the atomizer 26 to be vaporized creating an aerosol (which may comprise gaseous and liquid components) within the central passage 32. As the user continues to suck on the electronic smoking device 10, this aerosol is drawn through the central passage 32 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the atomizer 26 is converted into an aerosol more liquid is drawn into the atomizer 26 from the liquid reservoir 34, as described below with respect to FIG. 2, and thus is available to be converted into an aerosol through subsequent activation of the heating element 30.

Some electronic smoking devices are intended to be disposable and the electric power in the battery 18 is intended to be sufficient to vaporize the liquid contained within the liquid reservoir 34, after which the electronic smoking device 10 is thrown away. In other embodiments the battery 18 is rechargeable and the liquid reservoir 34 is refillable. In the cases where the liquid reservoir 34 is a toroidal cavity, this may be achieved by refilling the liquid reservoir 34 via a refill port. In other embodiments the atomizer/liquid reservoir portion 14 of the electronic smoking device 10 is detachable from the battery portion 12 and a new atomizer/liquid reservoir portion 14 can be fitted with a new liquid reservoir 34 thereby replenishing the supply of liquid. In some cases, replacing the liquid reservoir 34 may involve replacement of the atomizer 26 along with the replacement of the liquid reservoir 34. A replaceable unit comprising the atomizer 26 and the liquid reservoir 34 is called a cartomizer.

Figure 5A:
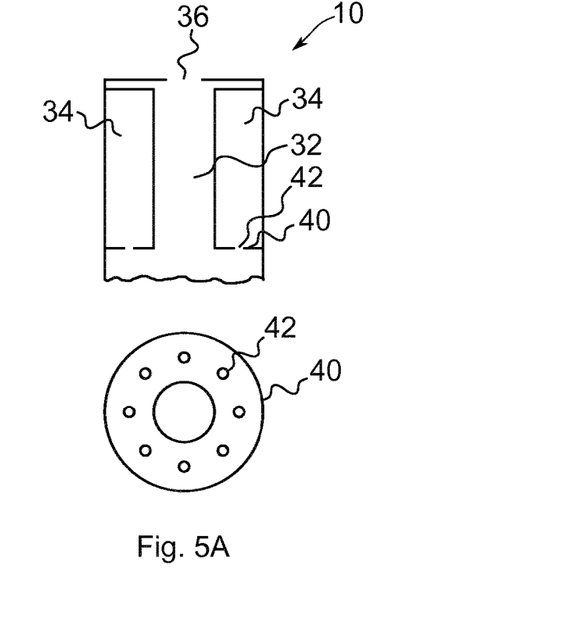
FIG. 5A is a partial cross-sectional view of the e-cigarette of FIG. 1 together with a top view of a base plate of the liquid reservoir.
Figure 5B:
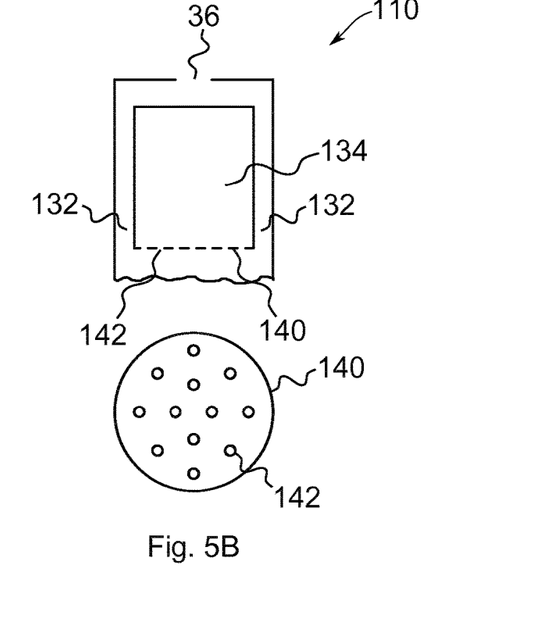
FIG. 5B is a partial cross-sectional view of the e-cigarette according to a second embodiment together with a top view of a base plate of the liquid reservoir.

The new liquid reservoir 34 may be in the form of a cartridge having a central passage 32 through which a user inhales aerosol. In other embodiments, aerosol may flow around the exterior of a cylindrical cartridge to an air inhalation port 36, as described in more detail with reference to FIG. 5B.

Of course, in addition to the above description of the structure and function of a typical electronic smoking device 10, variations also exist. For example, the LED 20 may be omitted. The airflow sensor 24 may be placed adjacent the end cap 16 rather than in the middle of the e-cigarette. The airflow sensor 24 may be replaced with a pus button or switch which enables a user to activate the electronic smoking device manually rather than in response to the detection of a change in air flow or air pressure.

Figure 3:
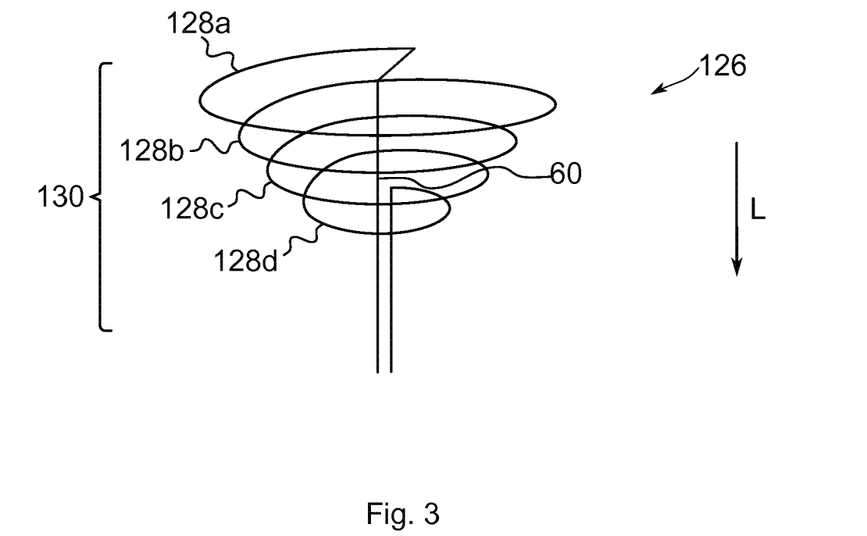
FIG. 3 is a perspective illustration of an atomizer according to a second embodiment.

Different types of atomizers may be used, as described below with reference to FIGS. 2 and 3.

FIG. 2 shows a partial perspective illustration of the atomizer 26 of FIG. 1. The heating element 30 has been omitted in FIG. 2 in order to simplify the understanding of the figure with respect to the remaining elements, in particular with respect to the first atomizer sections 28a, 28b, 28c, 28d, which can be seen in FIG. 2 through the opened-up casing 29. The first atomizer sections 28a, 28b, 28c, 28d are spaced apart from the casing 29, i.e. wall portions of the casing 29 are located at a predetermined distance from the first atomizer sections 28a, 28b, 28c, 28d. However, the casing 29 is optional and can be omitted.

The atomizer 26 comprises a plurality of first atomizer sections 28a, 28b, 28c, 28d, which, in the example shown, have the form of circular rings. The number of the first atomizer sections 28a, 28b, 28c, 28d can vary. The centers of the respective rings are located on a common central axis A that runs along the direction L. Different exemplary embodiments of first atomizer sections are shown in FIGS. 4A to 4E. Each of these first atomizer sections defines at least one opening that is at least partly encircled by the respective first atomizer section.

Figure 4A:
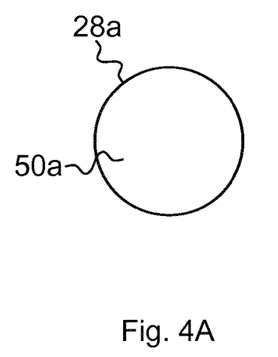
FIGS. 4A to 4E show various embodiments of first atomizer sections in top view.
Figure 4B:
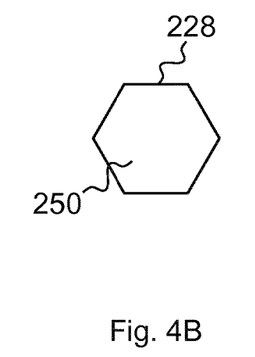
Figure 4C:
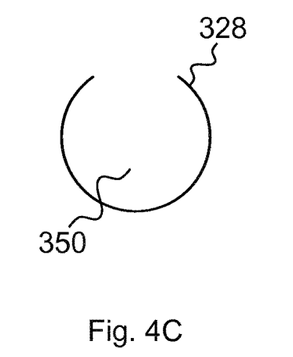

In FIG. 4A, the first atomizer section 28a of FIG. 2 is shown, where the circular ring completely encircles a circular opening 50a. FIG. 2B shows an alternative first atomizer section 228 in the form of a regular hexagon, which completely encircles a hexagonal opening 250. Instead of a hexagon, other polygons may be used, e.g. a trigon, a tetragon or an octagon. The respective polygons need not to be regular. In FIG. 4C, a first atomizer section 328 in the form of an open frame is shown, which defines an opening 350. This is to point out that a first atomizer section can define on opening both by a closed border, as shown in FIGS. 4A and 4B, and by an open border, as in FIG. 4C. In the latter case, the size of the opening 350 can be defined as the size of an area spanned between the legs of the open frame 328. The first atomizer section 428 in FIG. 4D defines a plurality of triangular openings 450, which have essentially the same shape and size. It is also possible that a first atomizer section defines multiple openings having different shape and/or size. FIG. 4E illustrates a further first atomizer section 428b defining multiple openings. The first atomizer section 428b of FIG. 4E results from a regular subdivision of the openings 450 of the first atomizer section 428a of FIG. 4D. The subdivision may also be irregular.

As shown in FIG. 2, the first atomizer sections 28a, 28b, 28c, 28d are spaced apart from each other along the direction L in which the atomizer 26 extends from the liquid reservoir (cf. FIG. 1) and respectively extend in a plane E that does not contain the direction L. In FIG. 2, the directions L is orthogonal to the plane E. Alternatively, the first atomizer sections 28*a*, 28*b*, 28*c*, 28*d* can be oriented mutually differently, i.e. can extend in different planes, in particular planes that need not be in orthogonal relation to the direction L in which the atomizer 26 extends from the liquid reservoir 34.

The respective distances between two of the first atomizer sections 28*a*, 28*b*, 28*c*, 28*d* can vary, depending e.g. on the size of the opening 50*a*, 50*b*, 50*c*, 50*d* defined by the respective first atomizer section 28*a*, 28*b*, 28*c*, 28*d* and/or on the kind of liquid supplied to the atomizer from the liquid reservoir 34, in particular dependent on the viscosity of the liquid.

Figure 4D:
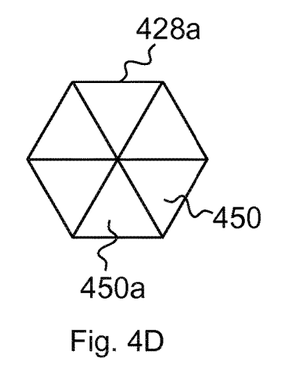
Figure 4E:
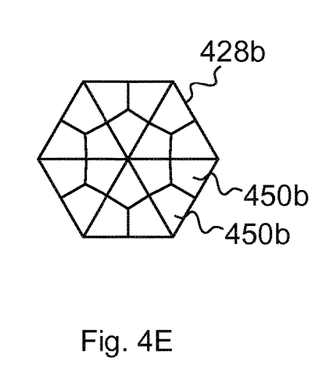

In general, the first atomizer sections 28*a*, 28*b*, 28*c*, 28*d*, as well as the first atomizer sections 228, 328, 428 shown in FIGS. 4*b* to 4D, are configured to hold liquid supplied from the liquid reservoir 34 by means of the surface tension of the liquid, before the liquid is aerosolized by means of a heating element 30. That is, liquid supplied from the liquid reservoir 34 to the atomizer 26 is received by the first atomizer section 28*a* that is located nearest to the liquid reservoir 34, i.e. adjacent to the openings 42 in the base plate 40 of the liquid reservoir. If the surface tension of the liquid is not sufficient so that the first atomizer section 28*a* cannot hold the liquid within the circular ring, the liquid will fall to the next first atomizer sections 28*b* having a smaller opening, i.e. a circular ring that has diameter that is smaller than the diameter of the circular ring 28*a*. Therefore, there is a chance that the first atomizer section 28*b* can hold the supplied liquid. If not, the liquid will fall to the next first atomizer section 28*c*, which again has an opening of smaller size, and so forth. Eventually, the liquid will be held by one of the first atomizer sections, by means of the surface tension of the liquid and a sufficiently small opening defined by the respective first atomizer section. In this way, a wicking effect can be provided so that, when liquid present in the atomizer 26 is converted into an aerosol by operation of the heating element, more liquid can be drawn into the atomizer 26 from the liquid reservoir 34 and thus is available to be converted into an aerosol through subsequent activation of the heating element 30. A conventional wick is therefore dispensable, i.e. the atomizer 26 is wickless. The wicking effect can be controlled by the size of the openings defined by the first atomizer sections, by the distance between the first atomizer sections, and by the viscosity of the fluid. The cone-shaped casing 29 may further help to guide the liquid inside the atomizer 26. Further parameters that can influence the supply of liquid to the atomizer 26 are the size and the number of openings 42 provided in the base of the liquid reservoir.

The first atomizer sections 28*a*, 28*b*, 28*c*, 28*d* are connected to each other by second atomizer sections 44. The second atomizer sections 44 essentially extend along the direction L in which the atomizer 26 extends away from the liquid reservoir 34. The second atomizer sections serve to stabilize the atomizer structure and to support the first atomizer sections 28*a*, 28*b*, 28*c*, 28*d*. The assembly including the first and the second atomizer sections is connected to the housing 29 by means of connecting elements 46 and 48, which connect the second atomizer sections 44 and the first atomizer sections 28*a*, 28*b*, 28*c*, 28*d* to the casing 29, respectively. In case there is no casing, the atomizer assembly can directly be connected to a side wall of the atomizer/liquid reservoir portion 14. The connecting structure can vary; connecting means 46 or 48 may be omitted.

As can be seen from FIGS. 1 and 2, an envelope of the atomizer 26 is cone-shaped, wherein an apex of the respective cone points in the direction L away from the liquid reservoir. Not only the internal atomizer structure including the first and second atomizer sections has a cone-shaped envelope, but also the casing 29 has a corresponding cone shape and respective wall portions of the casing 29 enclose the lateral surface of the internal atomizer structure.

As mentioned above, instead of circular first atomizer sections 28*a*, 28*b*, 28*c*, 28*d* polygonal first atomizer sections may be used, such as first atomizer sections 228 shown in FIG. 4B. In case the sizes of the respective openings defined by these polygonal first atomizer sections also decrease with increasing distance from the liquid reservoir, an envelope of the atomizer results that is pyramidal instead of cone-shaped. However, in order to assemble an atomizer, first atomizer sections can be used that have the same size, e.g. first atomizer sections 428*a*, 428*b* of the kind shown in FIGS. 4D and 4E, which may then be arranged as shown with respect to the first atomizer sections 28*a*, 28*b*, 28*c*, 28*d* in FIG. 2, i.e. spaced apart from each other along a central axis that extends in the longitudinal direction of the electronic smoking device. In order to obtain openings having decreasing sizes with increasing distance from the liquid reservoir 34, the openings of one level can further be subdivided, as exemplarily shown in FIGS. 4D and 4E. In other words, a cone-shaped or pyramidal envelope of the atomizer is an optional feature.

As already mentioned above, the atomizer 26 includes a heating element 30. In the embodiment discussed with reference to FIGS. 1 and 2, the heating element 30 is separate from the first atomizer sections 28*a*, 28*b*, 28*c*, 28*d*. According to a preferred embodiment, at least one of the first atomizer sections can form a part of the heating element. In other words, such a first atomizer section has different functions. On the one hand, it serves to receive and hold liquid supplied from the liquid reservoir. On the other hand, it serves to aerosolize the liquid. In this case, in addition to such first atomizer sections, an additional heating element part can be provided which is different from the first atomizer sections.

In FIG. 3 a respective embodiment of an atomizer 126 is illustrated in which all first atomizer sections 128*a*, 128*b*, 128*c*, 128*d* form part of the heating element 130. The atomizer 126 essentially comprises a helical coil with a plurality of turns, each of the turns corresponding to a first atomizer section 128*a*, 128*b*, 128*c*, 128*d*, respectively. Each turn can be interpreted as forming an open frame as shown in FIG. 4C. The diameters of the turns decrease with increasing distance form the liquid reservoir 34, given that the atomizer 126 is integrated in a respective electronic smoking device 10 as shown in FIG. 1 with respect to the atomizer 26 of FIG. 2. The heating element 130 further comprises a linear heating wire 60 that extends from the apex of the cone defined by the envelope of the atomizer 126 along a central axis of the cone. The linear heating wire further serves to stabilize the structure of the atomizer 126 and to enhance the above described wicking effect.

In FIG. 5A, a partial cross-sectional view of the electronic smoking device 10 of FIG. 1 is shown, together with a top view of a base plate 40 of the liquid reservoir 34. The base plate 40 is ring-shaped, due to the toroidal form of the liquid reservoir 34, and includes a plurality of openings or perforations 42 in order to supply liquid to the atomizer 26.

In FIG. 5B, a respective partial cross-sectional view of an electronic smoking device according to a second embodiment is shown, together with a top view of a respective base plate 140 of the liquid reservoir 134. In contrast to the embodiment shown in FIGS. 1, 5A, according to FIG. 5B the liquid reservoir 134 is cylindrical and air passages 132 are provided around the exterior of the respective cartridge. The base plate 140 of the liquid reservoir 134 is circular and also comprises a plurality of opening 142.

In summary, in one aspect the electronic smoking device includes a power supply portion comprising a power supply, an atomizer/liquid reservoir portion comprising a liquid reservoir storing a liquid, and an atomizer adapted to atomize the liquid stored in the liquid reservoir when operated by the power supply. The atomizer extends away from the liquid reservoir in a first direction, preferably in a longitudinal direction of the electronic smoking device, and comprises first atomizer sections. Each of the first atomizer sections defines an opening that is at least partly encircled by the first atomizer section. The sizes of the openings respectively defined by the first atomizer sections decrease with increasing distance of the first atomizer sections from the liquid reservoir in the first direction. The first direction can correspond to the longitudinal direction of the electronic smoking device.

According to an embodiment, the first atomizer sections are spaced apart from each other along the first direction.

According to an embodiment, wherein the first atomizer sections respectively extend in a plane not containing the first direction. The first direction can be essentially orthogonal to the plane.

According to an embodiment, the first atomizer sections are connected to each other by second atomizer sections, which can extend essentially along the first direction.

According to an embodiment, the first atomizer sections are configured to form ring-like sections or frame-like sections, wherein the frame-like sections can be open. Ring-like sections in particular include circular and oval sections as well as regular and irregular polygonal sections.

According to an embodiment, the first atomizer sections include a plurality of circular rings, wherein each of these rings has its center on a central axis running along the first direction and respectively extends in a plane that is essentially orthogonal to the axis. The diameters of the rings decrease with increasing distance from the liquid reservoir.

According to an embodiment, the first atomizer sections include a plurality of turns of a helical coil. The diameters of the turns decrease as the coil extends along the first direction away from the liquid reservoir.

According to an embodiment, an envelope of the atomizer is cone-shaped or pyramidal. An apex of the respective cone or pyramid points in the first direction away from the liquid reservoir.

According to an embodiment, the atomizer further comprises a heating element. In case an envelope of the atomizer is cone-shaped or pyramidal, the heating element can comprise a linear heating wire that extends from the apex of the cone or pyramid along a central axis of the cone or pyramid.

According to an embodiment, the atomizer further comprises a heating element, wherein at least one of the first atomizer sections forms a part of the heating element.

According to an embodiment, the atomizer further comprises a casing that at least partially encases the first atomizer sections. Wall portions of the casing are located at a predetermined distance from the first atomizer sections.

According to an embodiment, the electronic smoking device further comprises a perforated plate located at the side of the atomizer facing the liquid reservoir. The perforated plate is configured to supply liquid from the liquid reservoir to the atomizer through the perforations in the plate.

According to an embodiment, the perforated plate forms a base of the liquid reservoir, which base faces the atomizer.

Typically, the electronic smoking device is wickless.

According to another aspect, an atomizer for an electronic smoking device is provided. The atomizer is adapted to atomize liquid stored in a liquid reservoir of the electronic smoking device when operated by a power supply of the electronic smoking device. The atomizer, when integrated in the electronic smoking device, extends away from the liquid reservoir in a first direction, preferably in a longitudinal direction of the electronic smoking device. The atomizer comprises first atomizer sections, wherein each of the first atomizer sections defines an opening that is at least partly encircled by the first atomizer section. The sizes of the openings defined by the first atomizer sections decrease with increasing distance of the first atomizer sections from the liquid reservoir in the first direction.

Various embodiments of such an atomizer have already been described with respect to an atomizer of the electronic smoking device according to the first aspect.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS

10 electronic smoking device
12 power supply portion
14 atomizer/liquid reservoir portion
16 end cap
18 battery
20 light-emitting diode (LED)
22 control electronics
24 airflow sensor
26, 126 atomizer
28a, 28b, 28c, 28d, 128a, 128b, 128c, 128d, 228, 328, 428a, 428b first atomizer section
29 casing
30, 130 heating element
32 central passage
34, 134 liquid reservoir
36 air inhalation port
38 air inlets
40 perforated plate
42 perforation
44 second atomizer section
46, 48 connecting element
50a, 50b, 50c, 50d, 250, 350, 450a, 450b opening
52 air inlet opening
60 linear heating wire
132 passage

The invention claimed is:

1. An electronic smoking device comprising:
   a power supply portion including
      a power supply;
   an atomizer/liquid reservoir portion including
      a liquid reservoir configured to store a liquid, the liquid reservoir including a perforated plate located at the side of the liquid reservoir facing an atomizer, and further configured to supply liquid from the liquid reservoir to the atomizer through perforations in the perforated plate, the perforated plate forms a base of the liquid reservoir, and the atomizer extends away from the liquid reservoir in a first direction and is configured to atomize the liquid received from the perforated plate in the liquid reservoir when operated by the power supply, the atomizer includes a plurality of first atomizer sections spaced apart from each other along the first direction, each of the first atomizer sections form a circular ring that defines an opening, the size of the respective opening defined by each of the first atomizer sections decreases with an increasing distance of the first atomizer sections from the liquid reservoir in the first direction, a plurality of second atomizer sections extend between and connect the adjacent first atomizer sections to one another, a conical frustum casing that circumferentially extends about the plurality of first and second atomizer sections and is radially offset therefrom, wherein an apex of the conical frustum casing points in the first direction, away from the liquid reservoir, the conical frustum including a plurality of air inlet openings that extend radially relative to the first direction through the casing, and a plurality of connecting elements couple the second atomizer sections to the conical frustum casing.

2. The electronic smoking device of claim 1, wherein the first atomizer sections respectively extend in a plane not containing the first direction.

3. The electronic smoking device of claim 1, wherein each of the circular rings is centered on an axis running along the first direction and respectively extends in a plane that is orthogonal to the axis, and wherein the diameters of the circular rings decrease with increasing distance from the liquid reservoir in the first direction.

4. The electronic smoking device of claim 1, wherein the atomizer further includes a heating element with a linear heating wire that extends from the apex of the casing along a central axis thereof.

5. The electronic smoking device of claim 1, wherein the atomizer further includes a heating element, and at least one of the first atomizer sections forms a part of the heating element.

6. The electronic smoking device of claim 1, wherein a first of the first atomizer sections closest to the liquid reservoir is configured and arranged to receive a liquid from the liquid reservoir via the perforated plate, if the surface tension characteristics of the liquid is insufficient to hold the liquid on the first of the first atomizer sections, the liquid will descend to the next of the first atomizer sections having a smaller diameter than the first of the first atomizer sections; and wherein the next of the first atomizer sections is configured and arranged to hold the liquid where the smaller diameter facilitates liquids with lower surface tension characteristics than the first of the first atomizer sections.

7. The electronic smoking device of claim 1, wherein the electronic smoking device is configured and arranged to transfer the liquid from the liquid reservoir directly to the first atomizer sections of the atomizer without a wick.

8. An atomizer for an electronic smoking device, the atomizer comprising:

the atomizer configured to atomize liquid stored in a liquid reservoir of the electronic smoking device when operated by a power supply of the electronic smoking device, and when integrated in the electronic smoking device, to extend away from the liquid reservoir in a first direction;

a plurality of atomizer sections, wherein each of the atomizer sections defines an opening that is at least partly encircled by the first atomizer section, and the sizes of the openings defined by the atomizer sections decrease with increasing distance of the atomizer sections from the liquid reservoir, in the first direction, wherein the atomizer sections are each defined by a turn of a helical coil, wherein the diameter of each turn decreases as the helical coil extends along the first direction, away from the liquid reservoir; and a pair of linear heating wires extend from the closest and the furthest of the atomizer sections from the liquid reservoir along a central axis of the atomizer.

9. The atomizer of claim 8, wherein the atomizer further includes a casing that at least partially encases the atomizer sections, and the casing includes wall portions located at a predetermined distance from the atomizer sections.

10. The atomizer of claim 8, further including a conical frustum casing that circumferentially extends about the plurality of atomizer sections and is radially offset therefrom, the conical frustum casing including a plurality of air inlet openings that extend radially relative to the first direction through the casing.

11. The atomizer of claim 8, wherein the atomizer further includes an envelope that is cone-shaped or pyramidal, and an apex of the envelope points in the first direction, away from the liquid reservoir, and.

12. The atomizer of claim 8, wherein a first of the atomizer sections furthest from an apex of the helical coil is configured and arranged to receive a liquid from the liquid reservoir, if the surface tension characteristics of the liquid is insufficient for the liquid to be held on the first of the atomizer sections, the liquid will fall to an adjacent atomizer section of the plurality of atomizer sections having a smaller diameter than the first of the atomizer sections; and wherein the adjacent atomizer section is configured and arranged to hold the liquid where the smaller diameter facilitates liquids with smaller surface tension characteristics than the first atomizer section.

* * * * *